United States Patent [19]

Matsumoto et al.

[11] Patent Number: 5,144,022
[45] Date of Patent: Sep. 1, 1992

[54] METHOD OF PRODUCING POWDERY HIGH HLB SUGAR FATTY ACID ESTER

[75] Inventors: Shusaku Matsumoto, Kyoto; Yoshio Hatakawa, Higashiosaka; Akihiko Nakajima, Kyoto, all of Japan

[73] Assignee: Dai-Ichi Kogyo Seiyaku Co., Ltd., Japan

[21] Appl. No.: 516,512

[22] Filed: Apr. 30, 1990

[30] Foreign Application Priority Data

May 9, 1989 [JP] Japan .................. 1-116466

[51] Int. Cl.$^5$ .................. C07H 13/02; C07H 11/00
[52] U.S. Cl. .................. 536/119; 536/115
[58] Field of Search .................. 536/119, 1.1; 260/264

[56] References Cited

U.S. PATENT DOCUMENTS

| | | | |
|---|---|---|---|
| 2,948,716 | 8/1960 | Davis | 536/119 |
| 3,792,041 | 2/1974 | Yamagishi et al. | 536/119 |
| 4,298,730 | 11/1981 | Galleymore et al. | 536/119 |
| 4,898,935 | 2/1990 | Nakamura et al. | 536/119 |
| 4,966,966 | 10/1990 | Wada et al. | 536/119 |

FOREIGN PATENT DOCUMENTS

| | | |
|---|---|---|
| 0348883 | 1/1990 | European Pat. Off. |
| 1291365 | 3/1962 | France |
| 809815 | 3/1959 | United Kingdom |
| 1332190 | 10/1970 | United Kingdom |

*Primary Examiner*—Ronald W. Griffin
*Assistant Examiner*—L. Leary
*Attorney, Agent, or Firm*—Stevens, Davis, Miller & Mosher

[57] ABSTRACT

The present invention provides a new method of purifying a high HLB sugar fatty acid ester without using any solvent and giving it as a powdery form, in which a crude sugar ester is neutralized in pH value, and added with water, a neutral salt and sugar to give a sediment; this sediment is washed with acidic water; the washed water containing the high HLB sugar fatty acid ester at higher concentration is added with a fatty acid to separate a deposition; and this deposition is neutralized and spray dried.

20 Claims, 3 Drawing Sheets water + total salt + total sugar = 100 (wt%)

monoester + diester + triester = 100 (wt%)

METHOD OF PRODUCING POWDERY HIGH HLB SUGAR FATTY ACID ESTER

BACKGROUND OF THE INVENTION

The present invention relates to an industrial method of producing high HLB sugar fatty acid esters.

At present, sugar fatty acid esters (hereinafter called also <<SE>> for short) useful for surfactants are industrially obtained by the reaction of sugar and higher fatty acid methyl esters of $C_8$ to $C_{22}$ in solvents (for example dimethyl formamide, dimethyl sulfoxide and the like) in the presence of suitable catalysts (the solvent method: Japanese Patent Publication No. Sho 35-13102) or by melting sugar together with fatty acid soaps without using solvents but using water and then acting the molten mixture upon higher fatty acid methyl esters in the presence of catalysts (the water medium method: Japanese Patent Publication No. Sho 51-14485).

However, according to these two kinds of synthetic method, impurities, such as unreacted sugars, unreacted fatty acid methyl esters, remaining catalysts, soaps, free fatty acids and volatile matter (the remaining reaction solvent) used in the above mentioned "the solvent method" of SE synthesis are contained in the reaction mixture in addition to the aimed SE and the impurities, of which contents exceed the regulation values, must be removed before the products are obtained. In particular, of the above described impurities, the removal of the remaining reaction solvents (volatile matter) in the former solvent method is remarkably important in view of the recent increasingly severe regulation.*

* According to the standard of the FDA in U.S.A., the permissible concentration of remaining dimethyl sulfoxide in SE is 2 ppm or less [Fed. Regist., 51(214), 40160-1].

So, in order to "remove the impurities such as the remaining and others from the crude SE", a large amount of organic solvents (for example butanol, toluene, methylethyl ketone, methyl acetate and the like; refer to Japanese Patent Publication No. Sho 42-11588, Sho 48-1-448 and the like) has been used but the use of such a large amount of solvents has led to the following remarkable disadvantages in the industrial production of SE.

1) The possibility of the explosion and fire;
2) The provision of explosion proof electric apparatus against the above 1);
3) The tight closure of the manufacturing apparatus against the above 1);
4) The provision of the fire resisting construction all over the building against the above 1);
5) The rise of fixed cost due to the above 2), 3), 4).
6) The rise of cost price due to the loss of the solvents;
7) The negative effect due to the remaining solvents in product SE;
8) The bad influences upon the health of workers and thus the rise of fixed cost due to said bad influences.

In view of such the circumstances, it has been strongly desired in the industrial field in question to develop an art of making the use of organic solvents unnecessary in the purification of SE.

It is true that the purification methods without utilizing organic solvents have been formerly investigated experimentally and the following representative methods have been known.

1) The method of sedimenting SE with an acidic aqueous solution [British Patent 809,815 (1959)];

2) The method of sedimenting SE with an aqueous solution of general neutral salts (Japanese Patent Publication No. Sho 42-8850); and the like.

But if for example an aqueous solution of hydrochloric acid is added to a reaction mixture, as in the method 1), although SE is immediately sedimented, unreacted sugar is easily decomposed and transformed into glucose and fructose. Even though the main operation is conducted at low temperatures (0° to 5° C.), the decomposition can not be avoided. Thus, the recovery and reuse of the unreacted sugar become remarkably difficult.

In addition, even though the aqueous solution of neutral salts, such as sodium chloride and sodium sulfate, is added to the reaction mixture, SE is immediately sedimented as in the method 2). In this case, the unreacted sugar is not decomposed but monoesters in SE, which are useful ingredients are more soluble in water than other diesters, triesters and so on in SE are dissolved in a water phase side, so that not only the loss is increased but also the obtainment of sugar fatty acid esters (hereinafter referred to also<<high HLB-SE>>) having the high HLB value *, which are in particular recently great demand and the object of the present invention, is hindered.

* The hydrophile-lipophile balance having a value within a range of about 1 to 20. The larger this value is, the stronger the hydrophilicity is.

Furthermore, according to the more recent Japanese Patent Application Laid-Open No. Sho 51-29417, the property of separating the mixture solution of water and "purification solvents" (called in this manner is particular for discriminating from the reaction solvents) into a light liquid layer (a solvent phase side=upper layer) and a heavy liquid layer (a water phase side=lower layer) is used for the purification. That is to say, since in general a large quantity of water is contained in the heavy liquid layer (a water phase side=lower layer), the hydrophilic unreacted sugar, salts resulting from the catalysts and the like are dissolved in the heavy liquid layer (a water phase side=lower layer) while since a large quantity of purification solvents is contained in the light liquid layer (a solvent phase side=upper layer), the substances, such as SE, fatty acids and unreacted fatty acid methyl esters, having low polarity are dissolved in this light liquid layer (a solvent phase side=upper layer). Accordingly, unreacted sugar, salts and the like in the heavy liquid layer (a water phase side=lower layer) can be separated from SE, fatty acid and unreacted fatty acid methyl esters in the light liquid layer (a solvent phase side=upper layer) by the phase separation.

In this case, the reaction solvents, such as dimethyl sulfoxide which is used in SE synthesis are dissolved in the lower heavy liquid layer (the water phase side=lower layer) but they are dissolved in also the upper light liquid layer (a solvent phase side=upper layer) inconveniently. In some cases, it is possible to remove the reaction solvents by this method from SE. With the aid of difference between the solubilities of the reaction solvents in the lower layer and upper layer, many times of this phase separation procedure) makes it possible to remove most of reaction solvents for example to 2 ppm of Dimethyl sulfoxide. However this procedure necessitates a remarkable large quantity of purification solvent for removing the reaction solvent perfectly and is expensive in industrial manufacturing of SE. Thus, the known SE purification method has some disadvantages as formerly mentioned, i.e. use of purification solvent, possibility of fire, cost of the exprosion electric apparatus, rise of fixed cost, negative effect due to the remaining solvents in product SE and bad influence upon the health of workers.

In order to improve the known purification method of crude SE industrially in the different manner from the above described, inventors have been researched for several years the use of mere water as purification solvent instead of organic solvent, and it is achieved commercially as opened here. New invented method is firstly characterized by the mere water use instead of organic solvent as purification solvent i.e. nonorganic solvent purification of crude SE. Such a method has been never developed commercially. It is required to purify crude SE capable of perfectly removing the reaction solvents without bringing about the loss of the sugars and the product SE with mere water.

Furthermore, a problem to be solved in order to make the purification of SE with mere water industrially possible occurs in the drying of SE resulting from the mere use of water as the purification solvents.

That is to say, in usual the mere water-contained SE to be dried here is an aqueous solution when the water-content is 80% or more and a slurry when the water-content is less than 80%. Such the mere water-contained SE exhibits a remarkably peculiar viscosity behavior that in general the viscosity rapidly rises from about 40° C. with a maximum value at about 50° C. and is rapidly reduced when the temperature exceeds 50° C. (refer to pages 103, 107, 108, <<The Story of Sugar Esters (1984)>> published by the applicant company). In addition, it is substantially practically impossible due to the remarkable foaming to evaporate water by heating in a vacuum. And, if the heating temperature is high and the time of contact with the heating member is long, not only the decomposition of SE and the strong coloring and caramellization occur and also the acid value rises by the free fatty acids increased by the decomposition of SE (refer to Japanese Patent Publication No. Sho 37-9966).

In particular, in the end stage of the evaporation of water, the SE itself has a tendency of foaming with remaining water due to its characteristics that the softening point or the melting point is low (for example the softening point of sugar monostearate is about 52° C. and the melting point of sugar distearate is about 110° C.) and this leads to the more difficult dehydration and drying of SE. In addition, also the remarkably higher latent vaporization heat (c.a. 500 Kcal/kg H$_2$O or more). The higher vaporization temperature of water and the like than those of the solvents lead to the more difficult dryability. Accordingly, also in the case where the so-called "flash type" drier, into which the SE slurry heated by steam is continuously supplied, flashed in the vacuum chamber, dehydrated and dried, the sufficient dehydration and drying is haunted by various kinds of difficulty as above mentioned and even though these difficulties can be overcome, the dehydrated and dried SE is kept under the molten condition by heating, and that a large number of steps, such as a step of taking the molten SE out of the drier, a step of cooling the taken-out molten SE until temperatures of the melting point or less to solidify by blowing cool air and the like and the final pulverization in the pulverizer, are required and there are not only the degradation of SE due to many procedure steps, but also the possibility of the dust explosion in the final pulverization step.

Accordingly, also the solution of the above described various kinds of problem resulting from the drying is an important step for realizing the purification according to the present mere water medium purification method of crude SE. Thus new invited method is 2ndly characteristic of improved SE drying manner different from known SE manufacturing method. Such a SE drying method has never been developed commercially.

SUMMARY OF THE INVENTION

It is, therefore, the problem to be solved by the present invention to develop an art of industrially obtaining purified powdery high HLB-SE capable of removing not only the unreacted sugar but also the remaining solvents, the salts by-produced from the catalysts and other impurities without using the purification solvents, whereby solving all problems resulting from the use of the purification solvents.

In order to achieve the above object present invention provide a method of producing powdery high HLB sugar fatty acid esters, which comprises adjusting pH value of a reaction mixture comprising unreacted sugar, unreacted fatty acid methyl ester, catalysts, soaps, fatty acids and volatile matter in addition to aimed sugar fatty acid esters to a neutral range; adding water, neutral salts and sugar to said reaction mixture to give sediments; washing the sediments with acidic water, and adding fatty acids to the washing liquid to separate depositions; neutralizing the depositions; and then spray drying the resultant.

DETAILED DESCRIPTION OF THE INVENTION

Figure 1:
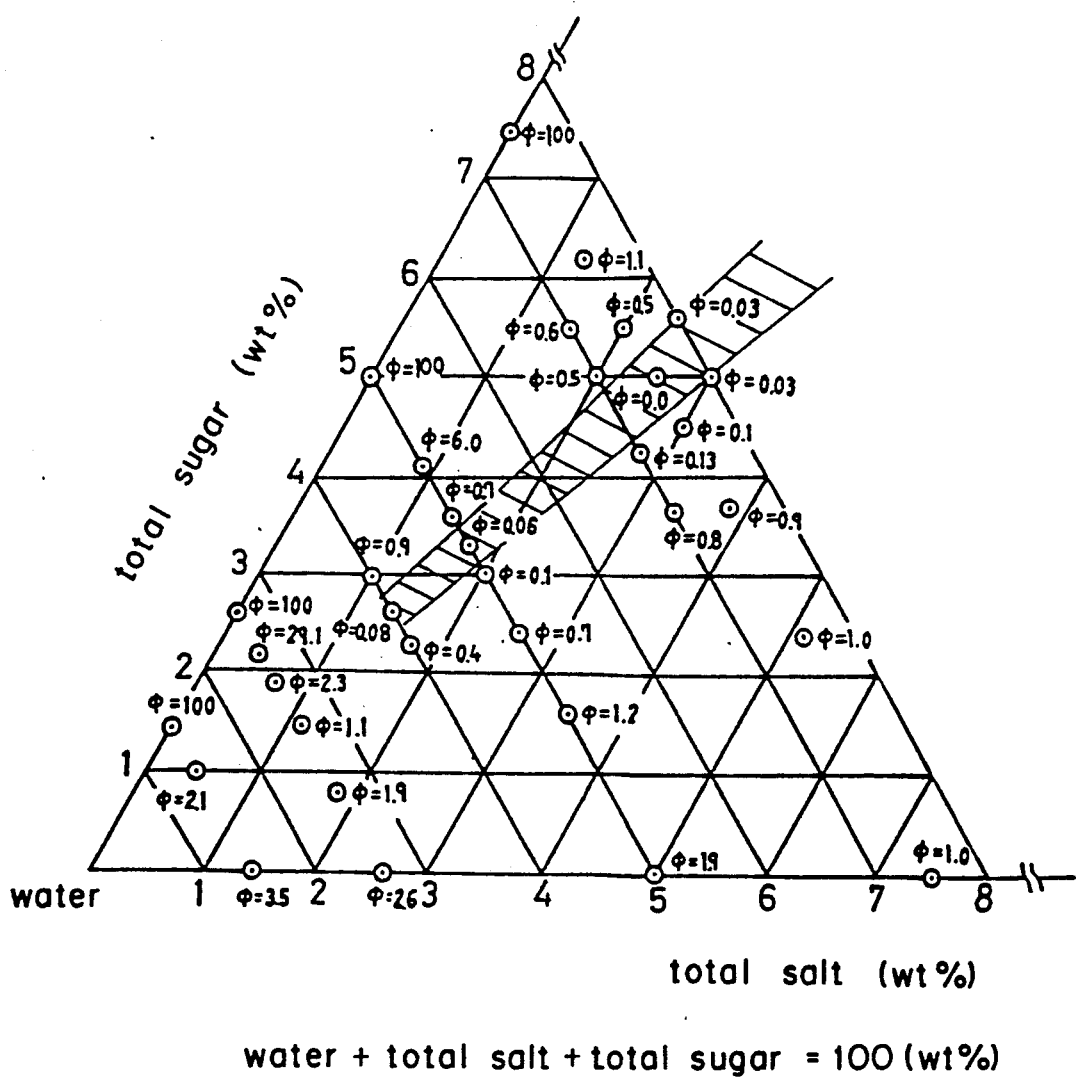
FIG. 1 is a ternary graph showing a solubility of SE ($\phi$) in the solution which contains water, sugar and salt. The composition of the solution is shown as sum quantity of the water, total sugar and total salts is 100 wt. % except SE quantity.

The present inventor has found it from his many experiments of the sedimentation with salts aiming at the solution of five points—(a) not only the quantity of the SE dissolved in the aqueous phase is surpressed at minimum but also said quantity is reduced to a zero to deposition the whole quantity of SE if possible; (b) the decomposition of the unreacted sugar is avoided; (c) the remaining reaction solvents (volatile matter) are dissolved in the aqueous phase to be separated from the SE sedimentation; (d) the sedimented SE is turned into powders under the purified condition; and (e) the unreacted sugar in the filtrate (or the top), from which the above described sedimented SE has been separated, is effectively recovered—that when sugar and neutral salts are dissolved in the aqueous solution of the reaction mixture under the suitable combinations of pH, temperature and composition of the neutral salts, sugar and water, not only the SE is not dissolved in the aqueous phase but almost the whole quantity thereof is sedimented but also both the volatile matter and the salts resulting from the catalysts, which are desired to be removed from SE, are dissolved in the aqueous phase in addition to the unreacted sugar. And, it has been found that even though the sedimented SE is dissolved in water again and then the reprecipitation process with the aqueous solution of neutral salts and sugar is repeated to remove impurities perfectly, the SE is not transferred in the aqueous phase but held under the sedimented condition and when acidic water having a suitable pH is added to this sediment to wash it, the high HLB SE fractions and soluble impurities in the remaining sediment are transferred in the acidic aqueous phase and the highly pure low HLB SE fractions are remained on the bottom as precipitates. It has been found also that it is industrially possible to recover and turn the high HLB-SE, which has been transferred in the aqueous phase, into powders by the addition of fatty acids and the use of the spray drying method. Thus, (1) the removal of the impurities from the SE reaction mixture and (2) the obtainment of the high HLB powdery SE and thus the classification of the SE depending upon its use from the SE reaction mixture have become industrially possible without using the organic solvents. These have been thought to be impossible and have never been expected from the prior arts.

The present invention is based on the above described knowledges and the main point of the present invention consists in that the pH of the reaction mixture comprising the unreacted sugar, the unreacted fatty acid methyl esters, the catalysts, the soaps, the fatty acids and the volatile matter in addition to the aimed sugar fatty acid esters is adjusted to a neutral range of pH, the sediments produced by adding water, the neutral salts and sugar to the reaction mixture separated sediment being washed with acidic water, the fatty acids being added to the washing acidic liquid to deposit High HLB-SE, the deposition being separated, and the resulting deposition being neutralized and then spray dried to produce the powdery high HLB sugar fatty acid esters.

Accordingly, the present invention comprises the following various steps:

(I) A step of removing the impurities from the crude SE reaction mixture (a step of sedimenting the crude SE with salts, sugar and water);

(II) A step of washing the impure SE sediments (a step of classifying);

(III) A step of recovering the high HLB-SE from washing liquid mentioned in above (II) by adding fatty acid (a step of depositing the high HLB-SE by the addition of the fatty acids); and (IV) A step of dehydrating and turning the recovered deposited high HLB-SE into powders (a step of spray drying).

Figure 3:
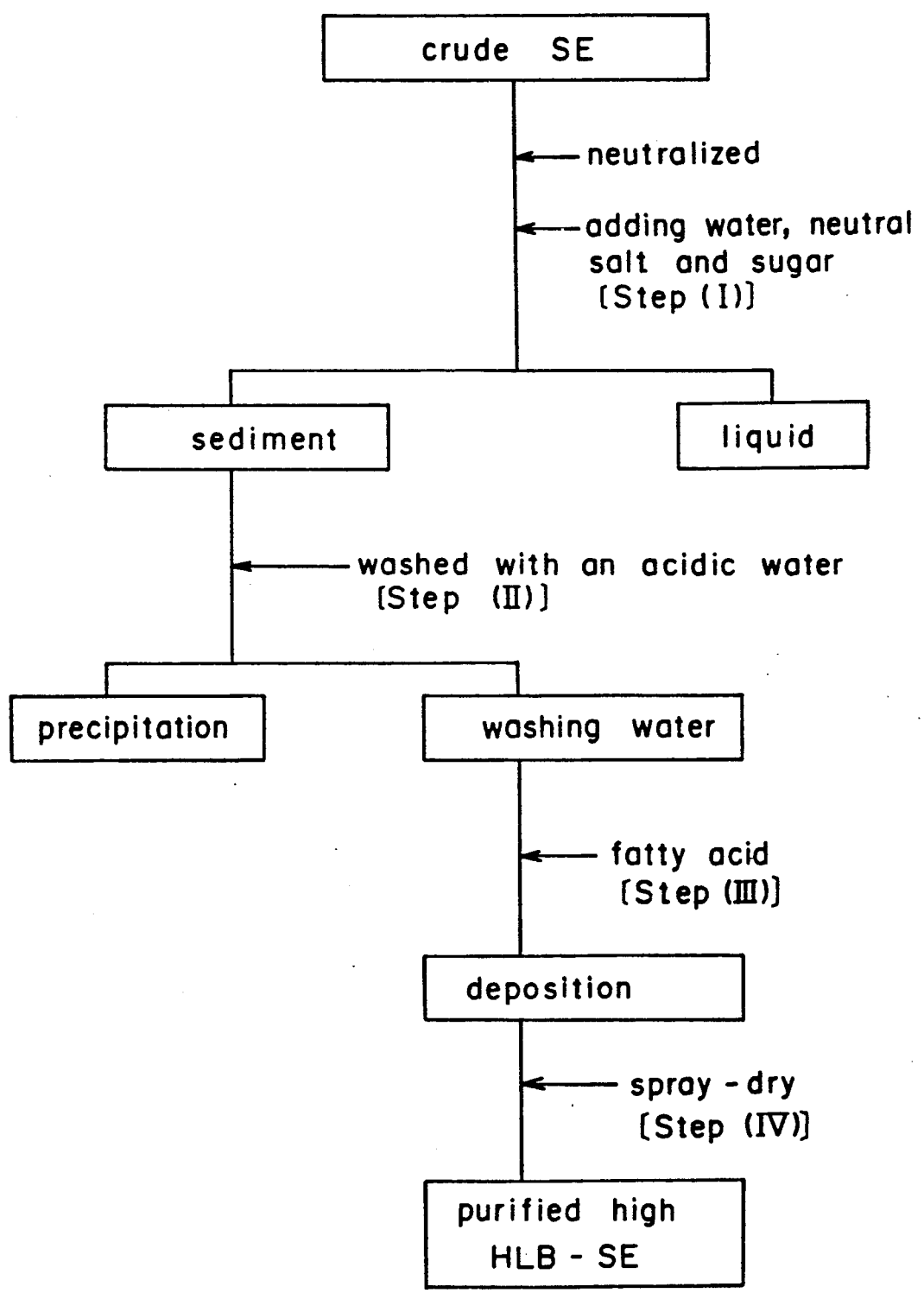
FIG. 3 is a flow chart illustrating a process of obtaining a purified high HLB-SE from a crude SE.

The process to purify the high HLB-SE from the crude SE is illustrated in FIG. 3.

The respective important matters relating to the present invention are below described.

Synthesis of the SE by the Solvent Method

In the synthesis of the SE by the solvent method, in usual, a mixture of sugar and fatty acid methyl esters is dissolved in a reaction solvent, for example dimethyl sulfoxide, several times the sum total quantity of said mixture in volume and the resulting solution is held at 80° to 90° C. for several hours at about 20 to 30 Torr in the presence of alkaline catalysts, such as potassium carbonate ($K_2CO_3$), to easily produce the SE reaction mixture in a reaction conversion % (based on the fatty acid methyl ester) of 90 or more.

Subsequently, in order to eliminate the activity of the alkaline catalysts in the SE reaction mixture, an equivalent quantity of organic acids, such as lactic acid and acetic acid, or mineral acids, such as hydrochloric acid and sulfuric acid, is added to the SE reaction mixture. The catalysts are turned into the neutral salts corresponding to potassium lactate and the like by this neutralization.

Finally, upon distilling away the reaction solvents, for example dimethyl formamide, in a vacuum, the crude mixture (the reaction mixture after the neutralization and distillation) having the composition within the nearly following range is obtained.

| | |
|---|---|
| Sugar fatty acid esters | 15–95% |
| Unreacted sugar | 1.0–80% |
| Unreacted fatty acid methyl esters | 0.5–10% |
| Neutral salts resulting from potassium carbonate | 0.05–7% |
| Soaps | 1.0–10% |
| Fatty acids | 0.5–10% |
| Volatile material (remaining reaction solvents) | 3.0–30% |

According to the above process SE obtained usually contains monoesters in a quantity of 10 to 75% (diesters or more are contained in a quantity of 90 to 25%). And, the fatty acid radicals mainly contained in the fatty acid methyl esters, the soaps and the fatty acids, respectively, are saturated ones and have a common number of carbon atoms of 16 to 22.

(1) A step of removing the impurities from the crude SE reaction mixture

Subsequently, water is added to the above described crude reaction mixture, so that a ratio of water to the crude reaction mixture may amount to 5:1 to 40:1, preferably 20:1, by weight and at the same time the pH of the resulting mixture is regulated so as to be 6.2 to 8.2, preferably 7.5.

In this time, if the ratio of water to the reaction mixture is outside of the above described range, for example it is less than 5, the viscosity of the resulting aqueous solution is increased and thus the following operations become substantially difficult to conduct. On the contrary, if it exceeds 40, the viscosity is reduced and thus the following operations become easy to conduct and also the aimed removal of the reaction solvents can be suitably conducted but a remarkably increased cost of energy is required for the removal of water in the recovery of the unreacted sugar and the like and thus the economy is lost.

Furthermore, it is desirable for the prevention of the decomposition of the aimed SE that the pH of the aqueous solution is adjusted at 6.2 to 8.2. If the pH is 8.2 or more, there is the possibility that the SE is stoichiometrically decomposed with alkalies. Even though the pH is 6.2 or less, if for example the aqueous solution is exposed to high temperatures of 90° C. or more, there is the possibility of the decomposition with acids.

Additionally neutral salts and sugar are added to the aqueous solution of the SE reaction mixture, which has been adjusted in pH in the above described manner, with maintaining the temperature at 50° to 80° C. as far as possible. In this time, it is preferable that the neutral salts to be added meet the following equation (3) at first.

[(weight of neutral salts to be added)+(weight of salts resulting from the catalysts)]/[(water content weight) +(total weight of salts)+(total weight of sugar)]=0.015 to 0.12 (by weight)   (3)

wherein the total weight of salts=(weight of neutral salts to be added)+(weight of salts resulting from the catalysts)   (4)

and the total weight of sugar=(weight of sugar to be added)+(weight of the unreacted sugar from the beginning)   (5)

Next, it is preferable that the weight of sugar to be added is determined by the equation (6).

[(weight of sugar to be added)+(weight of unreacted sugar from the beginning)]/[(water content (weight))+(total weight of salts)+(total weight of sugar)]=0.025 to 0.20 (by weight)   (6)

In addition, it is preferable that also the ratio of the total weight of salts to the total weight of sugar meets the following equation (7) in addition to the above described both equations.

(total weight of salts/total weight of sugar)=0.4 to 0.6, preferably 0.5   (7)

The present inventors have found that when the aqueous solution containing the SE sediments obtained by adding the neutral salts and sugar so as to meet the above described three equations (3), (6) and (7) together is heated to 50° to 80° C., almost nearly the whole quantity of SE is sedimented even though any one of lactates, acetates, sodium chloride and sodium sulfate is added as the neutral salts. This phenomenon is a peculiar one, which has not been known and has an important value for the object of the present invention. And, the skillful utilization of this fact leads to the transference of the following four kinds of ingredient into the aqueous phase and their separation from the cake of the sedimented SE (that is the slurry).

1) The whole sugar including the unreacted sugar (the sum total sugar);
2) The volatile matter;
3) The salts resulting from the catalysts; and
4) The neutral salts added.

Incidentally, since the solution is not acidic in this time, sugar is not decomposed and thus sugar can be easily recovered and reused in case of need.

The attached FIG. 1 is one of ternary graphs showing this phenomenon in more detail. Referring to FIG. 1, provided that the weight of the SE dissolved in the aqueous phase=$W_Y$[g] and the weight of the SE sedimented=$W_X$[g], the ratio of the weight of the SE dissolved in the aqueous phase to the sum total weight ($W_X+W_Y$) [g] of the SE $\phi$ [%] is defined by the following equation (8).

$$\phi = \{W_Y/(W_X+W_Y)\} \times 100 \ (\%) \quad (8)$$

It is shown by the triangular coordinates in FIG. 1 how $\phi$ is changed under the following conditions:

Temperature = 80° C., pH = 7.5;

| -continued |  |
|---|---|
| Water:reaction mixture = 7.4:1 (by weight); | |
| Fatty acid radical = stearic acid radical; | |
| Composition of the reaction mixture | |
| Sugar fatty acid esters | 29% |
| Unreacted sugar | 35% |
| Unreacted fatty acid methyl esters | 2% |
| Salts resulting from the catalysts | 1% |
| Soaps | 3% |
| Fatty acid | 1% |
| Volatile matter (remaining reaction solvents) | 29% |
| Distribution of esters in the SE: | |
| Monoester = 65%, diester and upper = 35%, | |
| Water content (weight) + the total weight of salts + the total weight of sugars = 100% (weight) | |

In FIG. 1, the total weight of salts and the total weight of sugars are the quantity defined by the equation (4) and (5), respectively. And, the shaded portion of FIG. 1 is a range meeting the equations (3), (6) and (7) discovered by the present inventors at the same time.

$\phi=0$ can be substantially held good, that is the approximately whole quantity of SE can be sedimented, by determining the quantities of the neutral salts and sugar dissolved so that $\phi$ may be put in this shaded portion and sugar, the volatile matter, the neutral salts and the like dissolved in the aqueous phase can be removed by filtrating or centrifugally separating the sedimented SE.

(II) A step of washing the impure SE sediments

The SE, which has been almost completely sedimented from the aqueous solution of the crude reaction mixture by adding the neutral salts and sugar in said step of sedimentation with salts, is under the hydrated condition, that is the slurry condition. This SE still includes impurities, such as the volatile matter, the salts, sugar and the like, although in a comparatively small quantity. The present inventors have found it from their earnest investigations about the method of purifying the impure slurry that the excellent result can be obtained by washing it with acidic water.

That is to say, the impurities are dissolved away by washing the above described impure SE slurry with acidic water, of which pH has been adjusted at 3.0 to 5.5. Here, for example the mineral acids, such as hydrochloric acid and sulfuric acid and the organic acids, such as acetic acid and lactic acid, can be suitably used but every edible acid can be used. In addition, the temperature of acidic water is preferably 10° to 40° C.

The impurities (that is the volatile matter, the whole sugar, the added neutral salts, the salts resulting from the catalysts and the like) to be removed from the cake side can be transferred into the aqueous phase by washing under such the conditions.

In the above described washing step, if the temperature of acidic water is 40° C. or more, not only there is the possibility of the decomposition of the SE with the acids but also the viscosity is increased to make the operation difficult when the operation is continued for a long time, for example several months. On the other hand, it is necessary for the maintenance of the low temperature of 10° C. or less to install a refrigerator with thinking little of the economy. Accordingly, it is usually desirable that the operation is conducted at 10° to 40° C., in particular temperatures close to room temperature.

In addition, since it is necessary to remove four kinds of ingredient, that is the volatile matter (reaction solvents), the unreacted sugar, the added neutral salts and the salts by-produced by the neutralization of the catalysts, contained in the cake so far as possible in this step of washing the SE cake with acidic water, it is desirable that the SE cake to be treated is finely cut in said acidic water until the particle sizes small as far as possible in order to make the impurity particles enclosed in said cake easily isolatable from the cake. This object can be efficiently achieved by means of the fractionalization apparatus, such as the dispersion mixer (for example <<Homomixer>> made by Tokushu Kiki Kogyo KK) and the homogenizer or the colloid mill (for example <<Micolloider>>), and the four kinds of ingredient, that is the volatile matter (reaction solvents), the unreacted sugars, the salts resulting from the catalysts and the neutral salts, are completely transferred into the acidic aqueous phase from the cake of the sedimented SE. In this time, the notable phenomenon that the high HLB SE begins to be dissolved in the aqueous side from the sediments occurs. The solubility of this high HLB-SE in water depends upon the factors, such as temperature and pH, of the system. For example, it is shown in the attached FIG. 2 at normal temperature and pH of about 3.5.

Here, since the high HLB-SE has the high solubility in water, it is temporarily called the <<water-soluble SE>> and marked with "Y". Y has the high HLB and thus exhibits the high water-solubility. Accordingly, Y is not precipitated even in the acidic aqueous solution but dissolved in it in the usual manner.

On the contrary, since the low HLB-SE has the low water-solubility, it has a tendency of being precipitated at appointed acidic concentrations of hydrogen ion. So, it is temporarily called the <<precipitated SE>> and marked with "X". X has the low HLB and thus it is apt to be precipitated from the acidic aqueous solution.

Figure 2:
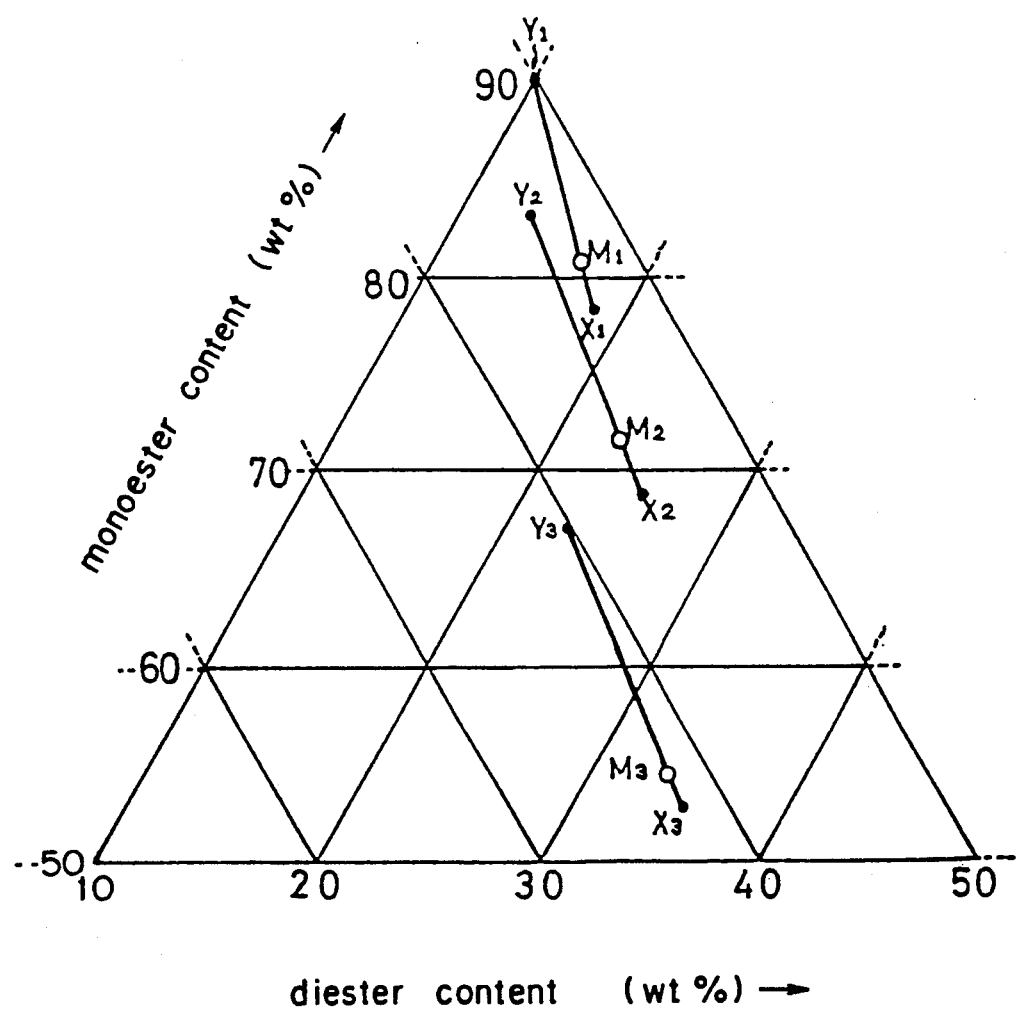
FIG. 2 is a ternary graph showing the High HLB-SE ester-composition of water phase side equilibrium to the low HLB-SE in deposition ester-composition of SE precipitation acidic water.

The above described FIG. 2 is a part of triangular coordinates in which the sum total of three ingredients—monoesters, diesters and triesters—is expressed by 100%. Referring to FIG. 2, the point M shows the composition of the original sample SE. The point X shows the composition of the low HLB precipitated SE. The point Y shows the composition of the high HLB water-soluble SE. The suffixes 1, 2, 3 show the SEs having different distributions of esters.

It is shown that provided that the aqueous solution having the pH of 3.5 is added to the sample SE having the distribution of esters of $M_2$ (monoesters=73%, diesters=22%, triesters=5%) in FIG. 2 so that the concentration of SE may be 3%, said SE is divided into said precipitated SE having the distribution of esters of $X_2$ (monoesters=68%, diesters=25%, triesters=7%) and the water-soluble SE having the distribution of esters of $Y_2$ (monoesters=84%, diesters=13%, triesters=3%).

The weights $WX_2$ and $WY_2$ of $X_2$ and $Y_2$ divided are calculated by working out the following equations (a), (b) in view of the property of the triangular coordinates.

$$WM_2 = WX_2 + WY_2 \qquad (a)$$

$$WY_2 \cdot \overline{Y_2M_2} = WX_2 \cdot \overline{X_2M_2} \qquad (b)$$

wherein $\overline{Y_2M_2}$ is a distance between the point $M_2$ and the point $Y_2$; $\overline{X_2M_2}$ is a distance between the point $X_2$ and the point $M_2$; $WM_2$ is a weight of $M_2$; $WX_2$ is a weight of $X_2$; $WY_2$ is a weight of $Y_2$ converted into a dry weight, respectively.

As above described, by skillfully utilizing the properties that the SE having the relatively high monoester-content (that is the high HLB-SE) is apt to be dissolved in the acidic water while the SE having the relatively low monoester-content (that is the low HLB-SE) is apt to exist on the precipitation, the SE can be quantitatively divided into the high HLB-SE and the low HLB-SE. It has been found also that in general the higher the monoester-content in the SE is, the more the quantity of the SE (Y) dissolved in water is, and vice versa. And, the quantity of the SE having an optional composition dissolved in the acidic water can be quantitatively determined by substituting the value of $\phi$ given by the data shown in FIG. 2 in the equations (a) and (b) to work out the values of WX and WY.

Thus, the acidic aqueous solution obtained in this washing step contains the high HLB-SE in a relatively large quantity, so that the high HLB-SE is separated from the precipitated SE mainly comprising the low HLB-SE by the filtration or the centrifugal separation. The obtained filtrate (or the top) contains, in addition to the high HLB-SE, a less quantity of remaining volatile matter (dimethyl sulfoxide and the like), salts, sugar and the like.

(III) A step of recovering the high HLB-SE from the washing liquid by adding fatty acid So, the present inventors have found it from their earnest investigations aiming at the obtainment of the high HLB-SE (in short the water-soluble SE) from the impure high HLB-SE-containing filtrate obtained by the above described washing step that this object can be effectively achieved by adding fatty acids to said filtrate.

It has been known that the SE can be associated in an aqueous solution under the appointed conditions to produce the high molecular congregate body having a micell structure (refer to page 102 in the above described publication).

By the way, as to the kinds of the SE, the SE, in which 1 to 3 fatty acid radicals are connected with oxygen atoms of three primary hydroxylic groups of a molecule of sugar, respectively, is called the monoester, diester and triester. And, as everyone knows, the monoester is superior to the diester and triester in hydrophilicity but inferior to the latter in formation of micells in water, so that the relatively low molecular SE micell congregate body (having a small molecular diameter) is formed. On the contrary, the diester and triester have the relatively low hydrophilicity but the remarkably high micell-formation capacity, so that they form the remarkably high molecular SE micell congregate body (having a large molecular diameter).

The present inventors have induced it from the above described fact that upon contacting the high HLB highly hydrophilic SE (in short the water-soluble SE containing the monoesters in a quantity exceeding about 80% with hydrophobic substances, such as fatty acids, in water, the SE micell congregate body having the micell structure different from the usual one is formed and the resulting congregate body is macro-sized to be already unable to exist in the form of an aqueous solution and at last the SE is combined with the fatty acids to be deposited. Supposing that this presumption is right, it ought to be expected that the water-soluble SE, which has been unable to easily separate by the usual methods, can be deposited in the industrial scale by skillfully utilizing this deposition phenomenon.

So, various kinds of investigation conducted on the basis of the above described idea led to the novel knowledge that the high HLB-SE is selectively deposited by the use of the fatty acids. This novel knowledge is below in detail described item by item.

(a) Deposition Phenomenon of the High HLB-SE by the Addition of the Fatty Acids

The present inventors have found an astonishing fact that the fatty acids are floating in the aqueous solution in the beginning but soon grown into the depositing condition or the molten condition and at last deposited in the bottom of the vessel when the fatty acids are added to the aqueous solution containing the water-soluble SE (monoesters in a quantity of 80% or more and thus diesters and triesters in a quantity of 20% or less in all) at temperatures of normal temperature to 90° C. and the pH of 3.0 to 5.5 in compliance with the above described assumption. These depositions collected in the bottom of the vessel were formed of a mixture comprising a large quantity of high HLB-SE and the fatty acids in a quantity nearly close to the quantity added. In addition, it has been successively found also that in general 1) the higher (within a range of normal temperature to 90° C.) the temperature of the aqueous solution is;

2) the lower (within a range of 3.0 to 5.5) the pH is;

3) the more (within an appointed certain range) the quantity of the fatty acids added is;

4) the larger (within a range of 1 to 4%) the concentration of the water-soluble SE dissolved is; and 5) the lower (at the monoester-content of 80% or more) the ratio of monoesters in the water-soluble SE is; the more the quantity of these depositions formed is.

As to the above described phenomena, the reason why the higher the temperature is, the more the quantity of the depositions is 1) is assumed to be the promotion of the combination of the SE with the fatty acids by the melting of the fatty acids. In fact, the quantity of the depositions is reduced to one severalth at the solid temperatures of the melting point or less. It is, however, desired that the temperature is low as far as possible in view of the stability of the SE against the temperature, so that it is not preferable that the temperature is heightened without any restriction. Accordingly, experimentally judging, the temperatures within the range of about 50° to 80° C. give the desirable result meeting both aspects of the quantity of the depositions and the stabilized maintenance of the SE. Incidentally, even alakynic acid of $C_{20}$ has the melting point of 77° C., so that this upper limit of temperature is not less than the melting points of the general fatty acids composing the SE.

The lower the pH is, the more the quantity of the sediments is 2). As everyone knows, the SE is remarkably stabilized in the acidic pH range rather than in the alkaline pH range. But, also in the case where the acidity is too strong, the stability of the SE is damaged, so that it is preferable to set the pH within the weakly acidic range, that is 3.0 to 5.5. Within such the pH range, the lower the pH is, the more the quantity of depositions formed is. In order to obtain a large quantity of deposition it is suitable taking other conditions into consideration that the pH is set within the weakly acidic range, that is about 3.5 to 4.0.

The quantity of the required fatty acids added is dependent upon the quantity and concentration of the water-soluble SE dissolved. Accordingly, strictly speaking, the quantity of the fatty acids added is not always correlated with the quantity of the depositions but there is the tendency that the quantity of the depositions is increased with an increase of the quantity of the fatty acids added in many cases.

However, the addition of an excessively large quantity of fatty acid generally leads to the increased quantity of the depositions formed and contrarily the increased quantity of fatty acid as the impurities, so that the undesirable effect occurs in that the purity of the obtained high HLB-SE is reduced.

In the case where the water-soluble SE (high HLB-SE) is dissolved in an excessively large quantity 4), both the viscosity and the specific gravity of the aqueous solution are too increased to separate the depositions.

So, for example, in the case where stearic acid is a constituent fatty acid of the SE, it is preferable in respect of the separation efficiency that the concentration of the water-soluble SE is set at about 2.0%.

In the case where the monoester-content of the SE is generally 80% or less 5), the water-solubility can not be maintained within the acidic pH range, whereby the monoesters are partially deposited. According to the present inventors' experiences, if the monoester-content is 80% or more (accordingly, diesters and triesters are contained in a quantity of 20% or less in total), the SE is water-soluble at the pH of about 3.5 to 4.0 in many cases. In the case where the monoesters are contained in a quantity of 90% or more, the SE maintains the water-solubility more surely and does not settle even within the acidic range of the above described extent.

Next, as to the quantity of the depositions, the SE containing monoesters in a less quantity (wherein the monoester-content >80%) formes the depositions in a more quantity. That is to say, there is the tendency that the larger the content of diesters and triesters is (wherein the content of diesters and triesters <20%), the more the quantity of the depositions is.

The above described knowledges lead to the following art of recovering the water-soluble SE.

(b) The Art of Recovering the Water-Soluble SE by the Addition of Fatty Acids

It has been industrially not easy to obtain the water-soluble SE (containing a large quantity of monoester and having a high HLB value) without using the solvents. But, the skillful utilization of the above described phenomena found by the present inventors leads to the prospected development of the novel industrial art of recovering the water-soluble high HLB-SE as depositions without using solvents by merely adding harmless substances (in short fatty acids).

The art of recovering the water-soluble high HB-SE mainly comprising stearic acid as the constituent fatty acids is below described but it goes without saying that this art is not limited by the addition of stearic acid. This art can be industrially put into practice also by adding other kinds of fatty acid. However, in order not to make the problem complicate, it is desirable that the fatty acids of the same kinds as the constituent fatty acids of the SE are added.

i) The acidic aqueous solution obtained in the pickling step of the crude SE product containing the high HLB-SE (water-soluble SE) contains a smaller quantity of remaining volatile matter), salts, sugar and the like in addition to a large quantity of high HLB-SE. This acidic aqueous solution is maintained at the pH of 3.0 to 5.5 and preferably heated to 50° to 80° C. to set the concentration of the SE contained at 1.0 to 4.0%, preferably 2%.

ii) The Quantity of Fatty Acids Added

Upon adding stearic acid (or fatty acids similar to stearic acid) to the above described acidic aqueous solution, the water-soluble SE having the high HLB value begins to cohere around fatty acids and at last it is combined with each other to form depositions. It is desirable that the quantity of fatty acids to be added is set within the following range:

[the weight of fatty acids added]/[the solid weight of the high HLB-SE (water-soluble SE)] = $\frac{1}{3}$ to 1/30

However, taking two points - the purity of the obtained high HLB-SE and the recovery rate of the high HLB-SE-into consideration, the preferable quantity of the fatty acids added is set within the following range:

[the weight of fatty acids added]/[the solid weight of the high HLB-SE (water-soluble SE)] = 1/12 to 1/20 iii) The pH of the Aqueous Solution

It has been above described that suitable acids must be added to the aqueous solution containing the aimed high HLB-SE to adjust the pH at 3.0 to 5.5 prior to the addition of the fatty acids but it is desirable in view of some points that the pH is adjusted at 3.5 to 4.0. In view of the stability of the SE, the pH within the excessive alkaline range should be avoided most. The SE is stable for a short time at the pH within the weakly acidic range (3.5 to 4.0). In addition, this pH range is preferable also in view of the increase of the quantity of the high HLB-SE (water-soluble SE) settled. In addition, if the pH is 3.5 to 4.0, there is little possibility that the apparatus for separating the formed depositions is corroded. (But, the use of hydrochloric acid and high-temperature sulfuric acid as the pH-adjuster should be avoided.)

Next, the aqueous solution having the weakly acidic pH is stirred to complete the deposition. The stronger stirring is preferable and the time of about 10 minutes is sufficient.

The thus separated depositions comprise water of about 80% and solid fractions of about 20%. The dried solid fractions, from which water has been removed, have the compositional ratio expressed by the following equation in many cases.

[the weight of the fatty acids]/[the weight of the high HLB-SE] = 1/10 to 1/20 iv) Washing of the depositions

The depositions obtained by combining the high HLB-SE deposited by the above described addition of the fatty acids with the fatty acids contain a smaller quantity of impurity, such as remaining volatile matter (for example DMSO as the reaction solvent), salts and sugar, in addition to water but these impurities are separated from the aqueous solution phase (the top) by successively washing with the acidic water and the content of the impurities (the volatile matter, salts, sugar and the like) is reduced, whereby improving the purity. In addition, the washing operation can be repeated additionally two or more times if desired, whereby the purity of the high HLB-SE is still more improved.

v) Recovery Rate 85 to 95% of the high HLB-SE, which has existed under the water-soluble condition in the beginning, can be recovered in the form of depositions by the above described operation. And, the resulting high HLB-SE-containing depositions containing solid fractions in a quantity of 5 to 20% are filtrated to be recovered and then neutralized and dissolved in water again followed by being transferred to the following step.

(IV) A step of dehydrating and turning the recovered deposited high HLB-SE into powders (a step of spray drying)

(a) Outline

It has been in detail described in [Prior Arts] that the industrial difficulties occur in the drying of the aqueous solution of sugar fatty acid esters. That is to say, the deterioration of the quality, such as the rise of the acid value of the SE, the coloring and the caramellization, can not be avoided on account of the properties, such as the viscosity characteristics and the low melting point, incidental to the SE is not only the case where a usual vacuum drier represented by the so-called "mixing type stirring drier" is used but also the case where the so-called "flash type drier", in which the SE slurry heated by steam is continuously supplied, flashed in the vacuum chamber, dehydrated and dried, is used. In addition, in the both cases, also the possibility of the dust explosion can not be neglected when cooled SE solid is pulverized.

However, the present inventors have found it from the results of their many experiments that the spray drying is optimum for the dehydration and drying of the above described high HLB-SE depositions and the disadvantages of the conventional drying means can be solved by one effort by the use thereof.

In this drying step, the water-containing high HLB-SE existing in the form of aqueous solution is continuously supplied to the spray drying tower through a pump to be divided into mist-like corpuscles by the spray by means of the nozzle or the centrifugal force of the rotary disk, whereby being brought into contact with the dry air current. Thereupon, the evaporation area of water is remarkably increased and thus the dehydration and drying can be finished in a remarkably short time (within several seconds from sprayed). Generally speaking, the rotary disk is more desirably used for spray-dry of the water-containing SE.

(b) Spray Drying Conditions

The temperature of the aqueous solution of the high HLB-SE can be optionally changed between 40° C. and 80° C. but it is desirable in view of the quality that it is selected within a range of 40° to 60 ° C.

In order to spray the above described solution or aqueous solution by means of the rotary disk, it is desirable that the rotation frequency is set at 15,000 to 24,000 rpm for the disk having a diameter of 5 to 10 cm.

Air to be sent to an inside of the tower should have at least a quantity of heat required for evaporating water contained in the solution or the aqueous solution. Accordingly, a larger quantity of air is required with a reduction of the temperature of air. In this time, the temperature of air may be set within a wide range of 10° to 100° C. but it is advantageous taking the drying efficiency and the prevention of the thermal decomposition of the aimed high HLB-SE into consideration that the temperature is selected from a range of 60° to 80° C.

Also the humidity of air to be sent to the inside of the tower has to do with the drying efficiency together with said temperature of air. It is economical that the operationally suitable absolute humidity is set within the following range:

Absolute humidity = 0.01 to 0.04 (Kg · water/Kg · dry air)

Various kinds of condition, such as a capacity, a diameter and a height, of the spray drying tower are designed on the premise of the above described spraying conditions. If the design and operational conditions of the tower are suitable, the powdery dry high HLB-SE containing water in a quantity of 5% or less can be continuously discharged from the lower portion of the spray drying tower. The resulting products are remarkably superior in quality due to the short thermal hysteresis thereof and the personnels for the drying operation are hardly demanded.

Operation

If acids are added to the high HLB-SE forming reaction mixture containing the unreacted sugar, the unreacted fatty acid methyl esters, the catalysts, the soaps, fatty acids and the volatile matter (remaining reaction solvents) to regulate the pH within the neutral range followed by adding water, the neutral salts and sugar to settle said impurities with salts at the suitable temperatures, the high HLB sugar fatty acid esters, the unreacted fatty acid methyl esters, the soaps and the fatty acids are settled and at the same time the volatile matter (remaining reaction solvents) are transferred to the aqueous phase side, so that the remaining volatile matter can be removed without using the organic solvents at all. In particular, the remaining solvents can be removed under the condition that the sugar fatty acid esters are not substantially lost at all by conducting the operation so that the conditions expressed by the equations (3), (6) and (7) may be satisfied. Then, the resulting sediments are washed with acidic water to separate the depositions brought about by adding fatty acids to the filtrate, whereby obtaining the high HLB sugar fatty acid esters containing solid fractions in a quantity of 5 to 20% from which the impurities, such as volatile matter, sugar, the neutralization of the catalysts, have been removed.

The resulting depositions are neutralized and spray dried to continuously produce the high HLB sugar fatty acid esters in the form of powders superior in color, odor, and fluidity and thus the powdery su9ar fatty acid esters having high HLB values can be industrially produced without using the solvents for use in the purification at all. In addition, in the above described pickling step, the sugar fatty acid esters remained in the precipitation are highly pure low HLB sugar fatty acid esters, so that also the object of separating the high HLB sugar fatty acid esters from the low HLB sugar fatty acid esters together with the purification of the crude sugar fatty acid esters can be achieved.

Preferred Embodiment

The practice and effects of the present invention are below described with reference to the preferred embodiment but it goes without saying that the preferred embodiment is illustrative and the present invention is not limited by the preferred embodiment.

EXAMPLE

The residue obtained by distilling away the reaction solvents from the sugar fatty acid ester reaction mixture by the solvent method having the composition shown in the following Table-1 was neutralized with lactic acid and then dried. The resulting dry matter of 100 Kg was dissolved in water of 1,000 Kg.

TABLE 1

| Ingredient | Weight (%) | Weight (Kg) |
|---|---|---|
| SE (stearate)* | 35.2 | 35.2 |
| Unreacted sugar | 37.5 | 37.5 |
| Unreacted fatty acid methyl esters (stearate) | 1.5 | 1.5 |
| Potassium lactate | 1.2 | 1.2 |
| Soaps | 2.1 | 2.1 |
| Stearic acid | 1.3 | 1.3 |
| DMSO** (volatile matter) | 21.2 | 21.2 |
| Total | 100.0 | 100.0 |

*Distribution of esters: monoesters 70%, diesters or more 30%
**Dimethyl sulfoxide (reaction solvent; hereinafter same)

Sugar of 62.5 Kg and a 50%-aqueous solution of potassium lactate of 97.6 Kg were added to the resulting aqueous solution and resulting mixture was heated until 75° C. to filtrate the settled cake which was dried at 80° C. in vacuum and then investigated on the composition with the results shown in the following Table-2. In this time, the water-content of the above described cake was 45%.

TABLE 2

| Ingredient | Weight (%) | Weight (Kg) |
|---|---|---|
| SE | 79.5 | 35.0 |
| Unreacted fatty acid methyl esters | 3.4 | 1.5 |
| Soaps | 4.8 | 2.1 |
| Fatty acids | 3.0 | 1.3 |
| DMSO | 2.5 | 1.1 |
| Sugar | 5.8 | 2.5 |
| Others | 1.0 | 0.5 |
| Total | 100.0 | 44.0 |

In addition, the quantity of the sugar fatty acid esters contained in the filtrate filtrated from the cake was measured by the gel percolation chromatographic (GPC) method (refer to page 63 in the above publication) with the result that the existence of the sugar fatty acid esters was not found at all and 95% of dimethyl sulfoxide as the reaction solvent was removed.

Subsequently, the cake (of 80 Kg) shown in the above Table-2 was suspended in a aqueous solution of acetic acid having normal temperature and the pH of 3.5 of 400 kg and then stirred for 10 minutes in a homomixer to filtrate fractionalized precipitates followed repeating the operation of washing the filtrate precipitates with the aqueous solution of acetic acid again four times in all. The composition of the obtained filtrate (pH=3.5) is shown in the following Table-3.

TABLE 3

| Ingredient | Weight (%) | Weight (Kg) |
|---|---|---|
| SE | 66.1 | 7.8 |
| Unreacted fatty acid methyl esters | 1.7 | 0.2 |
| Fatty acids | 4.2 | 0.5 |
| DMSO | 8.5 | 1.0 |

TABLE 3-continued

| Ingredient | Weight (%) | Weight (Kg) |
|---|---|---|
| Sugar and others | 19.5 | 2.3 |
| Total | 100.0 | 11.8 |
| Water | | 378.2 |
| Sum total | | 390.0 |

The pH of the aqueous solution (390 kg) shown in Table-3 was regulated at 3.5 and then the aqueous solution was heated until 80° C. followed by adding stearic acid of 0.78 kg and stirring for 10 minutes well. Upon stopping the stirring, water-containing depositions of 54.1 kg was separated from the top. Powders obtained by drying a part of the deposition had the composition shown in the following Table-4.

TABLE 4

| Ingredient | Weight (%) |
|---|---|
| High HLB-SE | 81.2 |
| Unreacted fatty acid methyl esters | 2.2 |
| Fatty acids | 12.2 |
| DMSO, sugar and others | 4.4 |
| Total | 100.0 |

Sodium hydroxide was added to the water-containing deposition having the composition shown in Table-4 of 54.0 kg drop by drop with stirring to regulate the pH at 7.8, whereby obtaining a neutral aqueous solution of high HLB sugar fatty acid esters.

Upon drying a part of this aqueous solution in vacuum, high HLB sugar fatty acid esters containing monoesters in a quantity of about 89.0% and having the composition shown in the following Table-5 were obtained.

TABLE 5

| Ingredient | Weight (%) |
|---|---|
| High HLB-SE* | 82.4 |
| Unreacted fatty acid methyl esters | 2.5 |
| Soaps | 7.5 |
| Fatty acids | 3.2 |
| DMSO | 4.4 |
| Total | 100.0 |

*Monoesters = 89.0%, diesters or more = 11.0%

In addition, the precipitates remaining after washing the sugar fatty acid esters having the composition shown in Table-2 with acetic acid to purify was low HLB sugar fatty acid esters containing monoesters in a quantity of 67%.

Finally, the neutral aqueous solution of high HLB sugar fatty acid esters, of which pH had been regulated at 7.8, was subjected to the spray drying under the following conditions:

| | |
|---|---|
| A diameter of the spray drying tower: | 2.0 m |
| A length of the straight cylindrical portion: | 1.5 m |
| A blast quantity: | 320 Nm³/hour |
| A diameter of the rotary disk: | 10 cm |
| A rotation frequency of the rotary disk: | 24,000 rpm |
| A temperature of air at the inlet: | 55.0° C. |
| An absolute humidity of air at the inlet: | 0.015 (kg.water/kg.dry air) |
| A supply rate of the slurry: | 1.3 kg/hour |

Powdery high HLB fatty acid esters obtained from the lower portion of the spray drying tower had the composition shown in the following Table-6, the water-content of 1.9% and the bulk specific gravity of 0.40 and exhibited no coloring, good odor and the superior fluidity.

TABLE 6

| Ingredient | Weight (%) |
|---|---|
| High HLB-SE* | 83.2 |
| Unreacted fatty acid methyl esters | 2.3 |
| Soaps | 7.3 |
| Fatty acids | 3.0 |
| DMSO, sugar and others | 4.2 |
| Total | 100.0 |

*Monoesters in the sugar fatty acid esters = 89.2%, diesters or more = 10.8%

That is to say, the high HLB sugar fatty acid esters containing monoesters in a quantity of 89.2% were obtained from the sugar fatty acid esters having the distribution of esters of monoesters=70.0% and diesters or more=30% in the reaction mixture in the beginning. In addition, the sugar fatty acid esters obtained from the pickled precipitates are the low HLB products containing monoesters in a quantity of 67%, as above described, so that the sugar fatty acid esters contained in the reaction mixture in the beginning were divided into the high HLB products and the low HLB products in the present Example.

What is claimed is:

1. A method of producing purified powdery high HLB sugar fatty acid esters, which comprises adjusting pH value of a reaction mixture comprising unreacted sugar, unreacted fatty acid methyl ester, catalysts, soaps, fatty acids and volatile matter, in addition to said sugar fatty acid esters, to a neutral range; adding water in a ratio of 5:1 to 40:1 by weight based on the weight of the reaction mixture, neutral salts and sugar to said reaction mixture to give sediments; washing the sediments with acidic water, and adding fatty acids to the washing liquid to separate depositions; neutralizing the depositions; and then spray drying the resultant.

2. A method as set forth in claim 1, wherein said reaction mixture has the following composition:

| | |
|---|---|
| Unreacted sugar | 1.0–80.0% |
| Unreacted fatty acid methyl esters | 0.5–10.0% |
| Catalysts | 0.05–7.0% |
| Soaps | 1.0–10.0% |
| Fatty acids | 0.5–10.0% |
| Volatile matter (reaction solvent) | 3.0–30.0% |
| Sugar fatty acid esters | 15.0–95.0% |

3. A method as set forth in claim 1, wherein said pH of the reaction mixture is adjusted at 6.2 to 8.2.

4. A method as set forth in claim 1, wherein said reaction mixture is heated to 50° to 80° C. after its adjustment of pH.

5. A method as set forth in claim 1 wherein the neutral salts and sugar are added to said reaction mixture, of which pH has been adjusted, so that the following relative expressions are satisfied:

(total weight of salts)/(water content by weight+total weight of salts+total weight of sugars)=0.015 to 0.12;

(total weight of sugars)/(water content by weight + total weight of salts + total weight of salts + total weight of sugars) = 0.025 to 0.20; and (total weight of salts)/(total weight of sugars) = 0.4 to 0.6 wherein the total weight of salts = weight of neutral salts to be added + weight of salts formed by neutralizing the catalysts and the total weight of sugars = weight of sugars to be added + weight of unreacted sugars from the beginning.

6. A method as set forth in claim 1 wherein the pH of the reaction mixture is adjusted using an acid selected from the group consisting of lactic acid, acetic acid, hydrochloric acid and sulfuric acid.

7. A method as set forth in claim 1 or claim 2, wherein the reaction mixture includes fatty acid radicals, mainly contained in the fatty acid methyl esters, soaps and fatty acids, respectively, which are commonly saturated fatty acid radicals of $C_{16}$ to $C_{22}$.

8. A method as set forth in claim 1 wherein the volatile matter (remaining reaction solvents) contained in the reaction mixture are dimethyl sulfoxide or dimethyl formamide.

9. A method as set forth in claim 1 wherein the neutral salts added to the reaction mixture are any one salt selected from the group consisting of sodium chloride, sodium sulfate, potassium lactate and potassium acetate.

10. A method as set forth in claim 1 wherein the content of monoesters in the sugar fatty acid esters is 10 to 75% (90 to 25% as for diesters or more).

11. A method as set forth in claim 1, wherein the pH of acidic water is 3.0 to 5.5.

12. A method as set forth in claim 1, wherein the pH of the washing liquid, to which the fatty acids have been added, is 3.0 to 5.5.

13. A method as set forth in claim 1 wherein the temperature of the washing liquid, to which the fatty acids have been added, is 50° to 80° C.

14. A method as set forth in claim 1 wherein said high HLB sugar fatty acid esters contain monoesters in a quantity of 80% or more (the sum total quantity of diesters and triesters is 20% or less).

15. A method as set forth in claim 1, wherein the concentration of said high HLB sugar fatty acid esters contained in said washing liquid, to which the fatty acids have been added, is 1 to 4%.

16. A method as set forth in claim 1, wherein the fatty acid is identical with or similar to the constituent fatty acid of the sugar fatty acid esters.

17. A method as set forth in claim 1, wherein fatty acids are added in a quantity of ¼ to 1/30 times that of said high HLB sugar fatty acid esters dissolved in said washing liquid to which the fatty acids are added.

18. A method as set forth in claim 1, wherein a solid content of the slurry to be spray dried is 4 to 40%.

19. A method as set forth in claim 1, wherein the humidity and the temperature of air to be blasted during the spray drying are set so that the following expression may hold good:

Absolute humidity = 0.008 to 0.05 [water (kg)/dry air (kg)]

wherein the temperature is 10.0° to 100.0° C.

20. A method as set forth in claim 1, wherein the powdery high HLB sugar fatty acid esters as the product have the following composition:

| | |
|---|---|
| Water | 0.5–5.0% |
| Unreacted fatty acid methyl esters | 0.5–10.0% |
| Soaps | 0.5–60.0% |
| Fatty acids | 0.5–10.0% |
| Sugar fatty acid esters | 98.0–15.0% |

* * * * *